(12) United States Patent
Benz et al.

(10) Patent No.: US 10,371,864 B2
(45) Date of Patent: Aug. 6, 2019

(54) (METH)ACRYLAMIDE POLYMERS FOR CONTACT LENS AND INTRAOCULAR LENS

(71) Applicant: Benz Research and Development Corp., Sarasota, FL (US)

(72) Inventors: Patrick H. Benz, Sarasota, FL (US); Adam Reboul, Sarasota, FL (US)

(73) Assignee: Benz Research and Development Corp., Sarasota, FL (US)

( * ) Notice: Subject to any disclaimer, the term of this patent is extended or adjusted under 35 U.S.C. 154(b) by 0 days.

(21) Appl. No.: 15/304,648

(22) PCT Filed: Apr. 17, 2015

(86) PCT No.: PCT/US2015/026371
§ 371 (c)(1),
(2) Date: Oct. 17, 2016

(87) PCT Pub. No.: WO2015/161199
PCT Pub. Date: Oct. 22, 2015

(65) Prior Publication Data
US 2017/0038500 A1    Feb. 9, 2017

Related U.S. Application Data

(60) Provisional application No. 61/981,684, filed on Apr. 18, 2014.

(51) Int. Cl.
| | | |
|---|---|---|
| *G02B 1/04* | (2006.01) | |
| *A61L 27/16* | (2006.01) | |
| *A61L 27/52* | (2006.01) | |
| *C08F 20/54* | (2006.01) | |
| *C08F 20/56* | (2006.01) | |
| *C08F 20/58* | (2006.01) | |
| *G02C 7/04* | (2006.01) | |

(52) U.S. Cl.
CPC ............ *G02B 1/043* (2013.01); *A61L 27/16* (2013.01); *A61L 27/52* (2013.01); *C08F 20/54* (2013.01); *C08F 20/56* (2013.01); *C08F 20/58* (2013.01); *G02B 1/041* (2013.01); *G02C 7/049* (2013.01); *A61L 2430/16* (2013.01)

(58) Field of Classification Search
CPC .................................................... G02B 1/043
See application file for complete search history.

(56) References Cited

U.S. PATENT DOCUMENTS

| 5,311,223 A * | 5/1994 | Vanderlaan ........... C08F 220/26 |
| | | 351/159.33 |
| 5,532,289 A | 7/1996 | Benz et al. |
| 6,011,081 A | 1/2000 | Benz et al. |
| 6,555,598 B2 | 4/2003 | Benz et al. |
| 8,026,326 B2 | 9/2011 | Benz et al. |
| 8,425,599 B2 | 4/2013 | Shadduck |
| 8,535,376 B2 | 9/2013 | Altmann |
| 2009/0176909 A1 | 7/2009 | Benz |
| 2011/0166247 A1* | 7/2011 | Myung ................... C08L 33/02 |
| | | 523/106 |
| 2011/0166831 A1 | 7/2011 | Benz et al. |
| 2011/0230589 A1* | 9/2011 | Maggio ................. C07F 7/0854 |
| | | 523/107 |
| 2012/0029111 A1* | 2/2012 | Chang .................. C08G 77/388 |
| | | 523/107 |
| 2012/0283353 A1 | 11/2012 | Mahadevan et al. |
| 2013/0096273 A1 | 4/2013 | Benz et al. |
| 2013/0253159 A1 | 9/2013 | Benz et al. |
| 2013/0317132 A1* | 11/2013 | Scales .................... G02B 1/043 |
| | | 523/107 |

FOREIGN PATENT DOCUMENTS

| JP | 62-169813 A | 7/1987 |
| JP | 2005-036181 A | 2/2005 |
| TW | 201408704 A | 3/2014 |

OTHER PUBLICATIONS

International Search Report and Written Opinion dated Aug. 25, 2015 in PCT/US2015/026371 (12 pgs.).
Office Action dated Oct. 18, 2018 in related Taiwanese Appl. 104112480 with partial English-language translation (7 pgs.).
Office Action dated Feb. 20, 2019 in related Japanese Appl. 2016-563083 with English-language translation (7 pgs.).

* cited by examiner

*Primary Examiner* — Michael F Pepitone
(74) *Attorney, Agent, or Firm* — Foley & Lardner LLP (57) ABSTRACT

An contact lens or intraocular lens (IOL) with very high water content polymers that have increased hydrolytic stability to withstand high temperatures such as autoclave temperatures, 123 C or even higher temperatures while in an aqueous environment comprising at least one polymer comprising one or more monomeric subunits comprising a polymerized acrylamide or methacrylamide group, at least one side group comprising an aliphatic carbon moiety substituted by at least one hydroxyl moiety, wherein the one or more monomeric subunits comprising a polymerized acrylamide or methacrylamide group, at least one side group comprising an aliphatic carbon moiety substituted by at least one hydroxyl moiety, comprise at least 50 wt. % of the polymer.

29 Claims, 3 Drawing Sheets

(METH)ACRYLAMIDE POLYMERS FOR CONTACT LENS AND INTRAOCULAR LENS

CROSS REFERENCE TO RELATED APPLICATIONS

This application is a National Stage application of PCT/US2015/026371, filed Apr. 17, 2015, which claims priority to and the benefit of U.S. Provisional Patent Application No. 61/981,684, filed Apr. 18, 2014. The foregoing provisional and PCT applications are incorporated by reference herein in their entirety.

BACKGROUND

Hydrogel polymers have been used for many years for a wide variety of medical devices. Two types of medical devices where hydrogel polymers are particularly well suited and well established are soft contact lenses and intraocular lenses.

As water content of a hydrogel polymer increases, its properties change dramatically. The desired water content is driven by the polymers end use. Soft contact lens polymers have advantageous properties as the water content increases.

Comfort and oxygen permeability increase as water content of a contact hydrogel increases but almost all hydrogel polymers lose water when on the eye at a rate that increases with increasing water content. A typical soft contact lens polymer with a saturated water content of 60% will have only 54-55% water content after a few hours on the eye. This loss of water content creates instability whereas the fit becomes much tighter and lens comfortable to the user. Furthermore, the loss of water causes the refractive index to increase, thereby increasing the lens power. These are typical properties of almost all soft contact lenses and cause the lens to be less comfortable towards the end of the day or wearing cycle. One of the only commercially-available non-ionic soft contact lens polymers that do not lose water on the eye is hioxifilcon, a copolymer of 2-Hydroxyethyl-methacrylate and Glycerol Methacrylate. See, e.g., U.S. Pat. No. 5,532,289. This copolymer family can be effectively formulated for soft contact lenses with water content ranging from 49% to 66%. Glycerol Methacrylate homopolymer can reach 74-75% water content but generally has mechanical disadvantages when used in devices such as contact lenses. There is a need, however, for very high water content hydrogels, 70-85%, that exhibit high stability to water loss on the eye. There is also a need for very high water content polymers that have increased hydrolytic stability to withstand high temperatures such as autoclave temperatures, 123° C. or even higher temperatures while in an aqueous environment.

SUMMARY OF THE INVENTION

We have succeeded in producing high purity monomers of the embodied disclosure. While some of these monomers are known in the art, a commercially viable synthesis giving high purity monomer has been unavailable. We report here a synthetic procedure suitable to produce high purity monomers of these acrylamides and methacrylamides, and also the resulting polymers made from these monomers. These monomers are used to make homopolymers and various copolymers whose properties are advantageous for use in high water content soft contact lenses, intraocular lenses, and other medical devices and coatings for medical devices.

Embodiments described herein include, for example, monomers, polymers, lenses, intraocular lenses, contact lenses, blanks for lenses, contact lenses or intraocular lenses, and methods for making and methods of using compositions lenses, contact lenses or intraocular lenses and other medical devices and coatings for medical devices.

At least one advantage for at least one embodiment includes an improved increase in water content of the material.

At least one advantage for at least one embodiment includes an increased hydrolytic stability of the material at elevated temperatures while in an aqueous environment.

At least one advantage for at least one embodiment includes an increased dimensional stability of the material.

At least one advantage for at least one embodiment includes an increased biocompatability of the material in the human body.

Some embodiments provide a contact lens or IOL comprising at least one polymer comprising one or more monomeric subunits comprising a polymerized acrylamide or methacrylamide group, at least one side group comprising an aliphatic carbon moiety substituted by at least one hydroxyl moiety, wherein the one or more monomeric subunits comprising a polymerized acrylamide or methacrylamide group, at least one side group comprising an aliphatic carbon moiety substituted by at least one hydroxyl moiety, comprise at least 50 wt. % of the polymer. In at least one embodiment, the at least one polymer is a homopolymer. In at least one embodiment, the at least one polymer is a copolymer. In at least one embodiment, the side group comprises a branched or unbranched C2-10 aliphatic carbon moiety substituted by at least one hydroxyl moiety. In at least one embodiment, the side group comprises a branched or unbranched C3-5 aliphatic carbon moiety substituted by at least two hydroxyl moieties. In at least one embodiment, the contact lens or IOL has an equilibrium water content greater than about 60 percent by weight. In at least one embodiment, the contact lens or IOL has an equilibrium water content of about 80 percent or greater by weight. In at least one embodiment, the at least one polymer comprises greater than zero, but less than 5% of a polymerized di-functional (meth)acrylamide silicone unit. In at least one embodiment, the contact lens or IOL has a water balance of greater than 8 to about 25 relative to poly(2-hydroxylethyl methacrylate). In at least one embodiment, the contact lens or IOL has a water balance of about 15 to about 20 relative to poly(2-hydroxylethyl methacrylate). In at least one embodiment, the side group comprises a branched or unbranched C3-6 aliphatic carbon moiety substituted by at least two hydroxyl moieties. In at least one embodiment, the side group comprises a C3 aliphatic carbon moiety substituted by at least two hydroxyl moieties. In at least one embodiment, the side group is a 2,3-dihydroxylpropyl moiety. In at least one embodiment, the one or more monomeric subunits comprising a polymerized acrylamide or methacrylamide group, at least one side group comprising an aliphatic carbon moiety substituted by at least one hydroxyl moiety, comprise at least 75 wt. % of the polymer. In at least one embodiment, the one or more monomeric subunits comprising a polymerized acrylamide or methacrylamide group, at least one side group comprising an aliphatic carbon moiety substituted by at least one hydroxyl moiety, comprise at least 95 wt. % of the polymer. In at least one embodiment, the contact lens or IOL comprises at least 90 percent by weight of the polymer comprising one or more monomeric subunits comprising a polymerized acrylamide or methacrylamide group, at least one side group comprising an aliphatic carbon moiety substituted by at least one hydroxyl moiety. In at least one embodiment, the contact lens or IOL comprises at least 95 percent by weight of the polymer comprising one or more monomeric subunits comprising a polymerized acrylamide or methacrylamide, at least one side group comprising an aliphatic carbon moiety substituted by at least one hydroxyl moiety. In at least one embodiment, the contact lens or IOL has a hydrolytic stability that is greater than a hydrolytic stability of a contact lens or IOL comprising a polymerized acrylate or methacrylate group. In at least one embodiment, the contact lens or IOL has an equilibrium water content that is greater than an equilibrium water content of a contact lens or IOL comprising a polymerized acrylate or methacrylate group. In at least one embodiment, the contact lens or IOL has a chemical stability that is greater than a chemical stability of a contact lens or IOL comprising a polymerized acrylate or methacrylate group. In at least one embodiment, the contact lens or IOL is a cross-linked homopolymer of 2,3-dihydroxylpropyl (meth)acrylamide. In at least one embodiment, the polymer comprises a cross-linking monomer is a di(meth)acrylamide. In at least one embodiment, the crosslinking monomer is PEG di(meth)acrylamide. In at least one embodiment, at least one polymer comprising one or more monomeric subunits further comprises a UV absorbing monomer. In at least one embodiment, the at least one polymer comprising one or more monomeric subunits comprises from 90 to 99 wt. % of 2,3-dihydroxylpropyl (meth)acrylamide monomeric subunits. In at least one embodiment, the at least one polymer is a copolymer comprising a polymerized comonomer characterized in that the polymerized comonomer is less hydrophilic than a polymer comprising a polymerized comonomer of an acrylamide or methacrylamide group, at least one side group comprising an aliphatic carbon moiety substituted by at least one hydroxyl moiety.

Other embodiments provide for a contact lens or IOL blank, comprising a polymer formed from a mixture of monomers comprising a crosslinking monomer and greater than about 50 wt. % of 2,3-dihydroxylpropyl (meth)acrylamide. In at least one embodiment, the mixture of monomers comprises greater than about 90 wt. % of 2,3-dihydroxylpropyl (meth)acrylamide. In at least one embodiment, the crosslinking monomer is PEG di(meth)acrylamide. In at least one embodiment, the contact lens or IOL blank further comprises water. In at least one embodiment, the contact lens or IOL blank has a water balance of greater than 8 to about 25 relative to poly(2-hydroxylethyl methacrylate). In at least one embodiment, the contact lens or IOL blank has a water balance of about 15 to about 20 relative to poly(2-hydroxylethyl methacrylate). In at least one embodiment, the mixture of monomers further comprises a UV absorbing monomer. In at least one embodiment, the mixture of monomers comprises more than about 92 wt. % of 2,3-dihydroxylpropyl (meth)acrylamide. In at least one embodiment, mixture of monomers further comprises greater than zero, but less than 5 wt. % of a polymerized di-functional (meth)acrylamide silicone monomer.

Other embodiments provide for method of forming a contact lens or IOL, comprising: (a) polymerizing a mixture of monomers to produce a polymer comprising more than about 80 wt. % of incorporated 2,3-dihydroxylpropyl (meth)acrylamide, and (b) forming the polymer into the contact lens or IOL. In at least one embodiment, the polymer is a homopolymer. In at least one embodiment, the polymer is a copolymer. In at least one embodiment, the polymer comprises greater than zero, but less than 5% of a polymerized di-functional (meth)acrylamide silicone unit. In at least one embodiment, the contact lens or IOL has a hydrolytic stability that is greater than a hydrolytic stability of a contact lens or IOL comprising a polymerized acrylate or methacrylate group. In at least one embodiment, the contact lens or IOL has an equilibrium water content that is greater than an equilibrium water content of a contact lens or IOL comprising a polymerized acrylate or methacrylate group. In at least one embodiment, the contact lens or IOL has a chemical stability that is greater than a chemical stability of a contact lens or IOL comprising a polymerized acrylate or methacrylate group. In at least one embodiment, the polymer comprises a polymerized UV absorbing monomeric unit. In at least one embodiment, the mixture of monomers to produce a polymer comprising from 90 to 99 wt. % of 2,3-dihydroxylpropyl (meth)acrylamide.

Other embodiments provide for a method of forming a contact lens or IOL, comprising: (a) polymerizing a mixture of monomers in the presence of a non-reactive polar diluent to produce a polymer comprising greater than about 50 wt. % of incorporated 2,3-dihydroxylpropyl (meth)acrylamide; and (b) forming the polymer into the contact lens or IOL. In at least one embodiment, the non-reactive polar diluent is water. In at least one embodiment, the non-reactive polar diluent is present in an amount of 50 wt. % to 150 wt. % of the mixture of monomers. In at least one embodiment, the mixture of monomers in the presence of a non-reactive polar diluent also comprises one or more azo-initiators. In at least one embodiment, the mixture of monomers in the presence of a non-reactive polar diluent also comprises one or more cross-linking agents. In at least one embodiment, the mixture of monomers in the presence of a non-reactive polar diluent also comprises one or more (meth)acrylamide co-monomers. In at least one embodiment, the mixture of monomers in the presence of a non-reactive polar diluent also comprises one or more azo-initiators. In at least one embodiment, the polymer comprises greater than about 90 wt. % of incorporated 2,3-dihydroxylpropyl (meth)acrylamide. In at least one embodiment, the monomers in the presence of a non-reactive polar diluent are polymerized in a mold.

Other embodiments provide for a composition comprising a polymer formed from a mixture of monomers comprising greater than 90 wt. % dihydroxylpropyl (meth)acrylamide. In at least one embodiment, the mixture of monomers comprising greater than 95 wt. % dihydroxylpropyl (meth)acrylamide. In at least one embodiment, the polymer is a homopolymer. In at least one embodiment, the polymer is a copolymer. In at least one embodiment, the mixture of monomers comprises greater than zero, but less than 5 wt. % of a di-functional (meth)acrylamide silicone monomer. In at least one embodiment, the mixture of monomers comprises greater than zero, but less than 5 wt. % of a comonomer characterized in that the comonomer is less hydrophilic than dihydroxylpropyl (meth)acrylamide. In at least one embodiment, the mixture of monomers further comprises a UV absorbing monomer. In at least one embodiment, the mixture of monomers comprises an di(meth)acrylamide monomer. In at least one embodiment, the polymer further comprises water. In at least one embodiment, mixture of monomers further comprises greater than zero, but less than 5 wt. % of a polymerized di-functional (meth)acrylamide silicone monomer. In at least one embodiment, the polymer formed from a mixture of monomers in a non-reactive polar diluent. In at least one embodiment, the polymer formed from a mixture of monomers in water. In at least one embodiment, the polymer has a hydrolytic stability that is greater than a hydrolytic stability of a polymer comprising greater than 90 wt. % dihydroxylpropyl (meth)acrylate. In at least one embodiment, the polymer has an equilibrium water content that is greater than an equilibrium water content of a polymer comprising greater than 90 wt. % dihydroxylpropyl (meth) acrylate. In at least one embodiment, the polymer has a chemical stability that is greater than a chemical stability of a polymer comprising greater than 90 wt. % dihydroxylpropyl (meth) acrylate. In at least one embodiment, the polymer is a homopolymer. In at least one embodiment, the polymer is suitable for use in a contact lens or IOL. In at least one embodiment, the composition is a contact lens.

Other embodiments provide for an intraocular lens comprising at least one polymer comprising one or more monomeric subunits comprising a polymerized acrylamide or methacrylamide group, at least one side group comprising an aliphatic carbon moiety substituted by at least one hydroxyl moiety, wherein the one or more monomeric subunits comprising a polymerized acrylamide or methacrylamide group, at least one side group comprising an aliphatic carbon moiety substituted by at least one hydroxyl moiety, comprise at least 50 wt. % of the polymer. In at least one embodiment, the at least one polymer is a homopolymer. In at least one embodiment, the at least one polymer is a copolymer. In at least one embodiment, the side group comprises a branched or unbranched C2-10 aliphatic carbon moiety substituted by at least one hydroxyl moiety. In at least one embodiment, the side group comprises a branched or unbranched C3-5 aliphatic carbon moiety substituted by at least two hydroxyl moieties. In at least one embodiment, the intraocular lens has an equilibrium water content greater than about 60 percent by weight. In at least one embodiment, the intraocular lens has an equilibrium water content of about 80 percent or greater by weight. In at least one embodiment, the at least one polymer comprises greater than zero, but less than 5% of a polymerized di-functional (meth)acrylamide silicone unit. In at least one embodiment, the intraocular lens has a water balance of greater than 8 to about 25 relative to poly(2-hydroxylethyl methacrylate). In at least one embodiment, the intraocular lens has a water balance of about 15 to about 20 relative to poly(2-hydroxylethyl methacrylate). In at least one embodiment, the side group comprises a branched or unbranched C3-6 aliphatic carbon moiety substituted by at least two hydroxyl moieties. In at least one embodiment, the side group comprises a C3 aliphatic carbon moiety substituted by at least two hydroxyl moieties. In at least one embodiment, the side group is a 2,3-dihydroxylpropyl moiety. In at least one embodiment, the one or more monomeric subunits comprising a polymerized acrylamide or methacrylamide group, at least one side group comprising an aliphatic carbon moiety substituted by at least one hydroxyl moiety, comprise at least 75 wt. % of the polymer. In at least one embodiment, the one or more monomeric subunits comprising a polymerized acrylamide or methacrylamide group, at least one side group comprising an aliphatic carbon moiety substituted by at least one hydroxyl moiety, comprise at least 95 wt. % of the polymer. In at least one embodiment, the intraocular lens comprises at least 90 percent by weight of the polymer comprising one or more monomeric subunits comprising a polymerized acrylamide or methacrylamide group, at least one side group comprising an aliphatic carbon moiety substituted by at least one hydroxyl moiety. In at least one embodiment, the intraocular lens comprises at least 95 percent by weight of the polymer comprising one or more monomeric subunits comprising a polymerized acrylamide or methacrylamide group, at least one side group comprising an aliphatic carbon moiety substituted by at least one hydroxyl moiety. In at least one embodiment, the intraocular lens has a hydrolytic stability that is greater than a hydrolytic stability of a intraocular lens comprising a polymerized acrylate or methacrylate group. In at least one embodiment, the intraocular lens has an equilibrium water content that is greater than an equilibrium water content of a intraocular lens comprising a polymerized acrylate or methacrylate group. In at least one embodiment, the intraocular lens has a chemical stability that is greater than a chemical stability of a intraocular lens comprising a polymerized acrylate or methacrylate group. In at least one embodiment, the intraocular lens is a cross-linked homopolymer of 2,3-dihydroxylpropyl (meth)acrylamide. In at least one embodiment, the crosslinking monomer is PEG di(meth)acrylamide. In at least one embodiment, at least one polymer comprising one or more monomeric subunits further comprises a UV absorbing monomer. In at least one embodiment, the at least one polymer comprising one or more monomeric subunits comprises from 90 to 99 wt. % of 2,3-dihydroxylpropyl (meth)acrylamide monomeric subunits.

DETAILED DESCRIPTION OF THE PREFERRED EMBODIMENTS

All references cited herein are incorporated by reference in their entirety.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used herein, the term "polymer" refers to a composition that is formed by polymerizing one or more different monomers. The term "polymer" thus includes "homopolymers" formed from only one type of monomer, "copolymers" which are formed from two or more different monomers, "terpolymers" formed from at least three different monomers, and any polymer that is formed from at least one type of monomer and may be formed from one, two, three, four, or more different monomers.

(Meth)Acrylamide Polymer Compositions

Hydroxy-substituted Aliphatic Carbon (Meth)Acrylamide Monomers

The (meth)acrylamide monomers used in the polymers of the present embodiments include an acrylamide or methacrylamide group with at least one side group comprising an aliphatic carbon moiety substituted by at least one hydroxyl moiety. In some embodiments, the aliphatic carbon moiety of the side group contains from 2 to 10 carbon atoms, for example, 2, 3, 4, 5, 6, 7, 8, 9, or 10 carbon atoms. The aliphatic carbon moiety is substituted by at least one hydroxyl moiety. In some embodiments, the aliphatic carbon moiety is substituted by 1 or 2 or 3 or 4 hydroxyl moieties. In one embodiment the aliphatic carbon moiety is substituted by two hydroxyl moieties, which are substituted on the same carbon, or on adjacent carbon atoms. In one embodiment the aliphatic carbon moiety is substituted by three hydroxyl moieties, which are substituted on adjacent carbon atoms. In at least one embodiment, the aliphatic carbon moiety contains three to five carbon atoms, and is substituted by hydroxyl moieties on two to three of the carbon atoms.

In a preferred embodiment, the (meth)acrylamide is selected from 2,3-dihydroxypropyl (meth)acrylamide, 2,3, 4-trihydroxybutyl (meth)acrylamide, and [3-hydroxy-2,2-di (hydroxymethyl)propyl (meth)acrylamide.

In a preferred embodiment, the 2,3-dihydroxypropyl (meth)acrylamide, 2,3,4-trihydroxybutyl (meth)acrylamide, and [3-hydroxy-2,2-di(hydroxymethyl)propyl (meth)acrylamide is produce by a method that results in substantially pure monomer, which is suitable for use as a major component of a polymerization reaction, as described herein. For example, the (meth)acrylamide monomer may be produced at a purity of greater than 95, 96, 97, 98, 99, or 99.5 percent.

Polymers and Copolymers

Polymers of the disclosed embodiments include homo polymer, copolymers of two, three, four or more different monomers (e.g., biopolymers, terpolymers, and quaterpolymers).

In embodiment, the polymer comprises a backbone consisting of polymerized acrylamide or methacrylamide group.

In one embodiment, the polymer comprises one or more monomeric subunits comprising a polymerized hydroxy-substituted aliphatic carbon (meth)acrylamide monomer. For example, in one embodiment, one or more monomeric subunits comprising a polymerized acrylamide or methacrylamide group, at least one side group comprising an aliphatic carbon moiety substituted by at least one hydroxyl moiety. The one or more monomeric subunits can be one or more of the (meth)acrylamide monomers having at least one side group comprising an aliphatic carbon moiety substituted by at least one hydroxy moiety discussed previously. For example, in In some embodiments, the aliphatic carbon moiety of the side group contains from 2 to 10 carbon atoms, for example, 2, 3, 4, 5, 6, 7, 8, 9, or 10 carbon atoms. The aliphatic carbon moiety is substituted by at least one hydroxyl moiety. In some embodiments, the aliphatic carbon moiety is substituted by 1 or 2 or 3 or 4 hydroxyl moieties. In one embodiment the aliphatic carbon moiety is substituted by two hydroxyl moieties, which are substituted on the same carbon, or on adjacent carbon atoms. In one embodiment the aliphatic carbon moiety is substituted by three hydroxyl moieties, which are substituted on adjacent carbon atoms. In one embodiment, the aliphatic carbon moiety contains three to five carbon atoms, and is substituted by hydroxyl moieties on two to three of the carbon atoms.

In a preferred embodiment, the (meth)acrylamide is selected from 2,3-dihydroxypropyl (meth)acrylamide, 2,3, 4-trihydroxybutyl (meth)acrylamide, and [3-hydroxy-2,2-di (hydroxymethyl)propyl (meth)acrylamide.

In one embodiment, the polymer is a homopolymer comprising monomeric subunits comprising a polymerized acrylamide or methacrylamide group, at least one side group comprising an aliphatic carbon moiety substituted by at least one hydroxy moiety.

The one or more monomeric subunits can be one or more of the (meth)acrylamide monomers having at least one side group comprising an aliphatic carbon moiety substituted by at least one hydroxy moiety discussed previously. For example, the aliphatic carbon moiety of the side group contains from 2 to 10 carbon atoms, for example, 2, 3, 4, 5, 6, 7, 8, 9, or 10 carbon atoms. The aliphatic carbon moiety is substituted by at least one hydroxyl moiety. In some embodiments, the aliphatic carbon moiety is substituted by 1 or 2 or 3 or 4 hydroxyl moieties. In one embodiment the aliphatic carbon moiety is substituted by two hydroxyl moieties, which are substituted on the same carbon, or on adjacent carbon atoms. In one embodiment the aliphatic carbon moiety is substituted by three hydroxyl moieties, which are substituted on adjacent carbon atoms. In one embodiment, the aliphatic carbon moiety contains three to five carbon atoms, and is substituted by hydroxyl moieties on two to three of the carbon atoms.

For example, the polymer can be a homopolymer comprising polymerized 2,3-dihydroxypropyl (meth)acrylamide, 2,3,4-trihydroxybutyl (meth)acrylamide, or [3-hydroxy-2,2-di(hydroxymethyl)propyl (meth)acrylamide.

In another embodiment, the polymer is a copolymer comprising one or more monomeric subunits comprising a polymerized acrylamide or methacrylamide group, at least one side group comprising an aliphatic carbon moiety substituted by at least one hydroxy moiety. For example, the aliphatic carbon moiety of the side group contains from 2 to 10 carbon atoms, for example, 2, 3, 4, 5, 6, 7, 8, 9, or 10 carbon atoms. The aliphatic carbon moiety is substituted by at least one hydroxyl moiety. In some embodiments, the aliphatic carbon moiety is substituted by 1 or 2 or 3 or 4 hydroxyl moieties. In one embodiment the aliphatic carbon moiety is substituted by two hydroxyl moieties, which are substituted on the same carbon, or on adjacent carbon atoms. In one embodiment the aliphatic carbon moiety is substituted by three hydroxyl moieties, which are substituted on adjacent carbon atoms. In one embodiment, the aliphatic carbon moiety contains three to five carbon atoms, and is substituted by hydroxyl moieties on two to three of the carbon atoms.

For example, the polymer can be a homo- or co-polymer comprising polymerized 2,3-dihydroxypropyl (meth)acrylamide, 2,3,4-trihydroxybutyl (meth)acrylamide, and/or [3-hydroxy-2,2-di(hydroxymethyl)propyl (meth)acrylamide. In the case of a copolymer, the polymer may also comprise one or more other polymerized monomers.

In some embodiments, the copolymer can further comprise one or more di-functional (meth)acrylamide silicone unit. By way of non-limiting example, di-functional (meth)acrylamide silicone units can include 1,3-bis(3-methacrylamidopropyl)tetramethyldisiloxane and additional siloxane containing bis(meth) acrylamides, such as:

R = CH$_3$ or H
n = 1 to 20

The one or more di-functional (meth)acrylamide silicone unit can be present in the polymer in an amount of greater than zero to about 10 wt. %. For example, the one or more di-functional (meth)acrylamide silicone unit can be present in the polymer in an amount of 0.1, 0.5, about 1, about 2, about 3, about 4, about 5, about 6, about 7, about 8, or about 9 to about 10 wt. %, or 0.1, 0.5, about 1, about 2, about 3, or about 4, to about 5 wt. %. The one or more di-functional (meth)acrylamide silicone unit can be present in the polymer in an amount of about of 0.1, 0.5, about 1, about 2, about 3, about 4, about 5, about 6, about 7, about 8, or about 9 or about 10 wt. %.

In some embodiments, the polymer can further comprise one or more incorporated UV absorbing monomers. The UV absorbing monomer may comprise a (meth)acrylamide moiety by which the monomer is incorporated into the polymer. In another embodiment, the UV absorbing monomer comprises a moiety other than a (meth)acrylamide moiety by which it is incorporated into the polymer.

The UV monomer may be a monomer known in the art, or may be a (meth)acrylamide derivative, e.g., of a (meth) acrylate UV-absorbing monomer. For example, the UV-absorbing monomers, or (meth)acrylamide derivatives thereof, as disclose in U.S. application Ser. No. 13/619,043, which is hereby incorporated by reference in its entirety. The UV-absorbing compound may also be another compound generally known in the art for use in contact lenses or IOLs.

In some embodiments, the polymer can further comprise one or more monomeric subunits which are crosslinked subunits. Di-, tri- or multi-functional crosslinking agents known in the art may be employed. The crosslinked subunits can comprise a monomer comprising two, three, or more (meth)acrylamide moieties, which are incorporated into the polymer backbone.

The polymers can be prepared using conventional polymerization techniques known to those in the field of polymer chemistry. Crosslinkers may be employed in the polymerization reaction. For example, any crosslinking or di-, tri-functional monomer, can be used in effective amounts to give the desired crosslinking density, e.g., in a concentration range of 0 to about 10 wt. %, such as about 0.01 to about 4 wt. %, or in some embodiments from 0.5 to 3 wt. %, based on the weight of the polymer. Examples of suitable cross-linking agents include di-olefinic functional component or ethylene glycol di(meth)acrylate (EGDMA) or ethylene glycol di(meth)acrylamide. Generally, crosslinkers help to enhance the resulting polymer's dimensional stability.

In one embodiment, the crosslinker is a multifunctional polyethylene glycol (PEG) di(meth)acrylate or di(meth) acrylamide. In some embodiments, the polyethylene glycol (PEG) di(meth)acrylate or di(meth)acrylamide has an average M$_n$ of about 3200 to about 10000 or about 5000 to about 10000, or about 3700, or any other value within the range of about 3200 to about 10000. In some preferred embodiments, the crosslinker is ethylene glycol di(meth)acrylamide. Additional cross linking agents include, but are not limited to: Methylene bis (meth) acrylamide, Ethylene bis (meth) acrylamide, N,N'-(1,2-dihydroxyethylene) bis (meth) acrylamide, Hexamethylene bis (meth) acrylamide, PEG based bis (meth) acrylamides, 1,3-bis(3-methacrylamidopropyl)tetramethyldisiloxane, Additional siloxane containing bis (meth) acrylamides, such as:

R = CH$_3$ or H
n = 1 to 20

In some embodiments, the compositions include one or more crosslinker with three or more polymerizable functionalities (a multi-functional crosslinking agent). An example of a multi-functional crosslinking agent includes, but is not limited to, trimethylol propane tri(meth)acrylate or trimethylol propane tri(meth)acrylamide. Some embodiments include two or more tri-functional crosslinking agents or a multi-functional crosslinking agent and a di-functional crosslinking agent known in the art or incorporated herein by reference. Therefore, in some embodiments, the polymer compositions include both a di- and tri-functional crosslinking monomer.

In one embodiment, the only crosslinker used is a tri-functional crosslinker such as a tri-functional (meth)acrylamide crosslinker. In one embodiment, the only crosslinker used is a di-functional crosslinker such as a di-functional (meth)acrylamide crosslinker.

Co-Polymers

Co-monomers used to formulate the co-polymers of the present embodiments are not particularly limited so far as they provide the requisite functionality of the polymeric materials. In some embodiments, the co-monomer used to formulate the co-polymers includes a reactive (meth)acrylamide reactive group along with a non-reactive side chain. For example, monomers disclosed in the following patents/applications can be utilized in the present invention. In another embodiment, the monomers disclosed in the following patents/applications can be formulated with a (meth) acrylamide reactive group in place of the (meth)acrylate reactive group, and utilized in the present invention. The patents, which are incorporated by reference in their entirety are: U.S. Pat. Nos. 5,532,289, 6,011,081, 6,555,598 and 8,026,326, and US Pub. Nos. 20080242818, 20090176909, 20110166381, 20130096273, 20130253159, all of which are assigned to Benz Research And Development Corp.

Compositions/Amounts

In some embodiments, the polymers are comprised of 50 wt. % or greater of the one or more monomeric subunits comprising a polymerized acrylamide or methacrylamide group, at least one side group comprising an aliphatic carbon moiety substituted by at least one hydroxy moiety. For example, the polymers are comprised of 55 wt. %, 60 wt. %, 65 wt. %, 70 wt. %, 75 wt. %, 80 wt. %, 85 wt. %, 90 wt. %, 95 wt. %, 96 wt. %, 97 wt. %, 98 wt. % or 99 wt. % or greater of the one or more monomeric subunits comprising a polymerized acrylamide or methacrylamide group, at least one side group comprising an aliphatic carbon moiety substituted by at least one hydroxy moiety. For example, the polymer, IOL or contact lens will have, in some embodiments, 55 wt. %, 60 wt. %, 65 wt. %, 70 wt. %, 75 wt. %, 80 wt. %, 85 wt. %, 90 wt. %, 95 wt. %, 96 wt. %, 97 wt. %, 98 wt. % or 99 wt. % or greater of a monomeric subunits comprising a polymerized acrylamide or methacrylamide group, at least one side group comprising an aliphatic carbon moiety substituted by at least one hydroxyl moiety, wherein the one or more monomeric subunits comprising a polymerized acrylamide or methacrylamide group, at least one side group comprising an aliphatic carbon moiety substituted by at least one hydroxyl moiety, or at least two hydroxy moieties, e.g., monomeric subunits comprising polymerized (meth)acrylamide is selected from 2,3-dihydroxypropyl (meth)acrylamide, 2,3,4-trihydroxybutyl (meth)acrylamide, and [3-hydroxy-2,2-di(hydroxymethyl)propyl (meth)acrylamide in this amount.

Functional Properties

The polymers of the present embodiments generally have an equilibrium water content of about 60 percent or greater by weight, or about 65 percent or greater by weight, or about 70 percent or greater by weight, or about 75 percent or greater by weight, or about 80 percent or greater by weight. For example, the polymers of the present embodiments can have an equilibrium water content of 60 to about 70, 75, 80, 85 or 90 percent, or they may have an equilibrium water content of about 70 to about 75, 80, 85 or 90 percent, or they may have an equilibrium water content of about 75 to about 80, 85 or 90 percent. In one embodiment, the polymer has a water content of greater than 80 percent, but less than 90 percent.

In some embodiments, the polymers are comprised of the one or more monomeric subunits comprising a polymerized acrylamide or methacrylamide group, at least one side group comprising an aliphatic carbon moiety substituted by at least one hydroxy moiety in an amount sufficient to form a polymer with a an equilibrium water content of about 60 percent or greater by weight, or about 65 percent or greater by weight, or about 70 percent or greater by weight, or about 75 percent or greater by weight, about 80 percent or greater by weight or about 85 percent or greater by weight.

The polymers of the present embodiments generally have a water balance of about 8 to about 25 or about 15 to about 20 relative, relative to poly(2-hydroxyethyl methacrylate).

In some embodiments, the polymers are comprised of the one or more monomeric subunits comprising a polymerized acrylamide or methacrylamide group, at least one side group comprising an aliphatic carbon moiety substituted by at least one hydroxy moiety in an amount sufficient to form a polymer with a water balance of about 8 to about 25 or about 15 to about 20 relative, relative to poly(2-hydroxyethyl methacrylate). In a preferred embodiment, the one or more monomeric subunits is polymerized 2,3-dihydroxypropyl (meth)acrylamide, 2,3,4-trihydroxybutyl (meth)acrylamide, and/or [3-hydroxy-2,2-di(hydroxymethyl)propyl (meth) acrylamide.

Water balance is defined as the ratio of the time it takes a material to dehydrate by 10% of its water weight and the time it takes to return to saturation. Values are reported relative to p-HEMA (Polymacon, 38%), used as a control. It is important that ambient conditions for the test be maintained accurately, and that all samples are measured under the same controlled conditions. The specified conditions are 21° C., 40±5% RH. Furthermore, a high precision, calibrated balance (such as Sartorius, Mettler, etc.) with 0.0001 gram capability is used. The balance should be placed in a controlled temperature and relative humidity environment of 21.

For each material, a uniform thickness material is based on expansion factors to yield a final wet (uniform) thickness material of 0.1 mm. Finished dry material are cleaned and hydrated overnight in buffered saline solution. BENZ buffered saline solution is composed of 8.01 grams $NaHBO_3$, 2.47 grams of $H_3BO_3$, and 0.14 grams $Na_2B_4O_7:10\ H_2O$ in 1 liter of distilled water, with a pH=7.26 and an osmolarity of 295 mOs at 22.5° C.

Material Dehydration Procedure is achieved by removing a clean sample material from saline vial, securing the material on wire holder and blotting gently with a lint free paper, hanging the wire holder on a balance scale, weighing and recording the weight. Dehydrating the material by 10% of its total water weight, recording the weight and cumulative time every 20 seconds until the 10% weight loss is achieved. After the test is complete, returning the material to the saline flask, allow the material to rehydrate back to saturation and repeat the drying procedure at least 2 more times to obtain an average weight loss.

The Lens Rehydration Procedure is completed by removing a clean sample material from saline vial, securing the material on a wire holder and blotting gently with a lint free paper, hanging the wire holder on the balance scale and weighing the material to determine the weight of the saturated lens, recording the weight, allowing the material to dehydrate 10% of its water weight (saturated weight content submerge the lens in buffered saline for 10 seconds, removing the material from the saline, blotting gently with a lint free paper and weighing the material. This is followed by recording the weight and time hydrated, and after weight is recorded, re-submerging the material 10 more seconds, blotting and recording the weight and cumulative time hydrated. This procedure is continued until the saturated weight of the material is achieved, and the complete procedure is repeated 3 times to obtain an average weight gain.

The water balance ratio of a material is obtained by dividing the time (in minutes) to dehydrate 10% from saturation by the time (in minutes) to rehydrate from 90% of saturation. This ratio value is the compared to p-HEMA control.

The polymers of the present embodiments generally have a high level of chemical stability. For example, in some embodiments the polymers, or products made with the polymers, of the present disclosure are stable in an aqueous environment used to autoclave the polymer or the product derived therefrom (e.g. contact lens) at elevated temperatures (e.g., 123° C. or even higher). Thus, the polymers, or products made with the polymers, of the present disclosure resist hydrolytic degradation under autoclave temperatures.

Lenses

Polymers of the disclosed embodiments can be incorporated, or formed, into a lens suitable for use in or on an eye. For example, contact lenses or IOLs can be formed from the polymers of the disclosed embodiments.

Contact Lenses

Contact lenses, and method for making contact lenses are known in the art. For example, lenses of the present embodiments can be made by molding individual lenses or by molding, e.g., injection molding or curing the polymer in a lens mold, or by making a blank, which is then machined to the proper dimensions. Both procedures are well understood in the art.

A present embodiment also provides for a contact lens made at least partially from the present polymers. In one embodiment, the device is a soft contact lens.

IOLs

IOLs, and method for making IOLs are known in the art.

A present embodiment also provides for an IOL made at least partially from the present polymers.

A present embodiment also provides intraocular lenses made at least partially from the present polymers. Such intraocular lenses include an optic portion and optionally one or more haptic portions. Typically, the polymers of the embodiments will make up part or the entire optic portion of the intraocular lens. In some embodiments, the optic portion of the lens will have a core made from one of the present polymer surrounded by different polymer or material. Lenses in which the optic portion is made up of at least partially of one of the present polymers will usually also have a haptic portion. The haptic portion can also be made of polymer of the embodiments or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the embodiments. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The polymers of the present embodiments can be designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The polymers of the present embodiments can also be designed to mimic a healthy crystalline lens in a relaxed state. Such lenses would be understood by one of skill in the art, and are described in, e.g., U.S. Pat. Nos. 8,535,376, 8,425,599, 8,535,376, which are incorporated by reference. Such lenses can be formed by molding methods described herein or known in the art.

For instance, the intraocular lens can be any type of intraocular lens. One skilled in the art of intraocular lenses understands the functions of these portions of the intraocular lens.

The optic portion can be approximately 6 mm in diameter prior to hydration. The 6 mm diameter is fairly standard in the art, and is generally chosen to cover the pupil in its fully dilated state under naturally occurring conditions. However, other sizes are possible and the present embodiments are not limited to any particular diameter or size of intraocular lens. Furthermore, it is not necessary that the lens optic portion be circular; it could also be oval, square, or any other shape as desired.

The intraocular lens can further include one or more non-optical haptic components extending away from the outermost peripheral surface of the optic portion. The haptic components can be of any desired shape, for example, a haptic lip, graduated spiral filaments or flat plate sections and are used to support the lens within the posterior chamber of the eye. Lenses having any desired design configuration can be fabricated. Further, although two types of haptic designs are shown in the figures, the haptics can have configurations other than those illustrated. Should the intraocular lens include other components besides the optical and haptic portions, such other portions can be made of a polymer as are the haptic and optic portions, or if desired, another material.

The intraocular lenses of the embodiments may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present embodiments can be made of a generally physiologically inert soft polymeric material that is capable of providing a clear, transparent, refractive lens body even after folding and unfolding. In some embodiments, the foldable intraocular lens of the present embodiments can be inserted into any eye by injection whereby the mechanically compliant material is folded and forced through a small tube such as a 1 mm to 3 mm inner diameter tube. In one embodiment the small tube has an inner diameter of approximately 2.0 or 1.9 or 1.8 or 1.7 or 1.6 or 1.5 mm or less. In one embodiment the inner diameter is approximately 1.4 to 2.0 mm. In one embodiment, the inner diameter is approximately 1.8 mm, in another it is 1.6 mm. In one embodiment, the finished IOL lens is micro-injectable (e.g. able to be injected through a small tube that has an inner diameter of approximately 1.8 mm or 1.6 mm).

Methods of Manufacture of Compositions

The polymers of the present embodiments can be prepared by (a) polymerizing a mixture of monomers in the presence of a non-reactive polar diluent to produce a polymer. In some embodiments, the non-reactive polar diluent is selected from the group consisting of water, N-methyl pyrrolidone (NMP), N,N-dimethylformamide (DMF), tetrahydrofuran (THF), N-alkyl lactams, and combinations thereof. In one embodiment, the non-reactive polar diluent is water, N-methyl pyrrolidone (NMP), or a combination thereof.

Generally, the non-reactive polar diluent is present in an amount sufficient to produce a polymer suitable for use in a contact lens or IOL. For example, in some embodiments, the non-reactive polar diluent is present in an amount of 30 wt. % to 250 wt. %, or 50 wt. % to 150 wt. %, or 50 wt. % to 100 wt. % of the mixture of monomers. While the non-reactive polar diluent may be present in an amount greater than 250 wt. %, generally it is not cost effective to utilize such a large amount of solvent.

Usually, the mixture of monomers in the presence of a non-reactive polar diluent also includes an amount of a polymer initiator. Other forms of initiating polymerization (e.g., UV radiation) are known, and are not intended to be excluded from the disclosed embodiments. However, in a preferred embodiment, the mixture of monomers in the presence of a non-reactive polar diluent also comprises one or more azo-initiators. Preferred azo-initiators of the present embodiments, include water soluble and organic soluble azo initiators, such as Vazo 50 (water soluble initiator), Vazo 52 (organic soluble), Vazo 64 (AIBN), Vazo 67 (organic soluble), Vazo 88 (high temp organic soluble).

Furthermore, one or more of the cross-linking agent, co-monomer, UV absorbing monomer, di-functional (meth) acrylamide silicone monomer, or other monomer—as described above—may be present in the he mixture of monomers in the presence of a non-reactive polar diluent.

As described above, it may be useful to add crosslinking agents to enhance the resulting polymer's dimensional stability. It may also be advantageous to add UV absorbing compounds with the lens monomers prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the polymer, such as from 0.01 to about 1 percent by weight of the polymer.

In some embodiments, the polymer comprises greater than 50 wt. %, 60 wt. %, 70 wt. %, 80 wt. %, 90 wt. %, 95 wt. %, 96 wt. %, 97 wt. %, 98 wt. % or 99 wt. % of incorporated monomeric subunits comprising a polymerized acrylamide or methacrylamide group, at least one side group comprising an aliphatic carbon moiety substituted by at least one hydroxy moiety. In a preferred embodiment, the (meth) acrylamide is selected from 2,3-dihydroxypropyl (meth) acrylamide, 2,3,4-trihydroxybutyl (meth)acrylamide, and [3-hydroxy-2,2-di(hydroxymethyl)propyl (meth)acrylamide.

The polymerization reactions of the present embodiments can be carried out at a temperature and time suitable for forming a polymer. For example, in some embodiments, the temperature of the reaction is within the range of 40° C. to 80° C., and the length of the reaction is from 1 to 20 hours.

The polymerization can also be carried out with a low volume of diluent. In one embodiment, the amount of diluent is 0%, or greater than 0 but less than 10, 15, 20, 25, or 30 wt. % of the monomers present in solution. These low volume diluent reactions are preferably used in the formulation of a blank that can be machined into a device, such as a contact lens by methods known in the art. The low volume diluent reactions are preferably carried in a manner that provides for a slow polymerization. This procedure can be carried out by methods known in the art, such as providing an initiator with a high temperature for initiation and by varying the temperature at which the polymerization reaction is performed.

In addition, the polymers of the present embodiments can be formed in a cast mold, such as a contact lens mold. The components used to form the polymer (e.g., various monomers, imitators, crosslinkers, and/or diluent) are added to the mold, and the mold assemblies are placed into an oven and cured at a temperature within 40° C. to 80° C., preferably 60° C. for 1 to 20 hours, preferably 10 hours. It is understood that the temperature and time of the curing can be altered based on the composition of the components used to form the polymer (e.g., amount of diluent), and the temperature and time of the curing provided herein are not limiting to the disclosure of the present embodiments.

Polymer does not Comprise Components

In one embodiment, the polymer backbone does not comprise any polymerized component other than (meth) acrylamide moieties.

In one embodiment, the polymer backbone does not comprise any polymerized (meth)acrylate moieties.

In one embodiment, the polymerization is not conducted "neat," i.e., without a solvent.

In one embodiment, the polymer does not comprise an ionic moiety.

Applications

One application is the use of the embodied polymers in lenses, including lenses adapted for the human eye, including IOLs and contact lenses.

Additional embodiments are provided in the following non-limiting working examples and contrasted with comparative examples.

WORKING EXAMPLES

The following abbreviations are used:
DHPAm=dihyroxypropylacrylamide
DHPMAm=dihyroxypropylmethacrylamide
EOEAm=ethoxyethylacrylamide
HPMAm=hydroxypropylmethacrylamide
Am=Acrylamide
DMA=dimethylacrylamide
HMBMAm=hexamethylene bis methacrylamide
MBAm=methylene bis acrylamide
Si=silicone bis methacrylamide
PEG3700=3700MW PEG bis acrylamide
MPAm=methoxypropyl acrylamide
HMAm=hydroxymethyl acrylamide
HEMA=hydroxyethylmethacrylate
NMP/DI is 95%/5% for V50 solubility Example 1

Formulation of Acrylamide Monomer

-continued

To a 1-L reactor charged 565 ml of anhydrous methanol under dry air flow, 3-amino-1,2-propanediol (from TCI, 50 g, 0.55 mol, 1 eq) was added portion-wise and stirred until fully dissolved (clear colorless solution). MEHQ (6 mg) and Sodium Carbonate (34.3 g) were added and the reactor was cooled (under vigorous stirring and air flow) to −10° C.

Acryloyl chloride (60.5 g, 0.67 mol, 1.2 eq) was added drop-wise over 2 h allowing temperature to slowly rise to +8° C., resulting in white milk-like suspension. The cooling bath was removed and temperature was raised to ambient (15-25° C.) over 1 h.

The resulting solids were filtered off and washed with methanol. The mother liquor was concentrated on a rotovap below 30° C. to approximately 100-150 ml volume. This residue was mixed with 0.5 L of acetonitrile (forming heavy bottom layer) and stirred for several hours.

The upper layer was decanted and concentrated to approximately ⅓ volume and diluted with 0.5 L of acetonitrile, followed by filtration through a pad of 40 g of silica gel.

Figure 1:
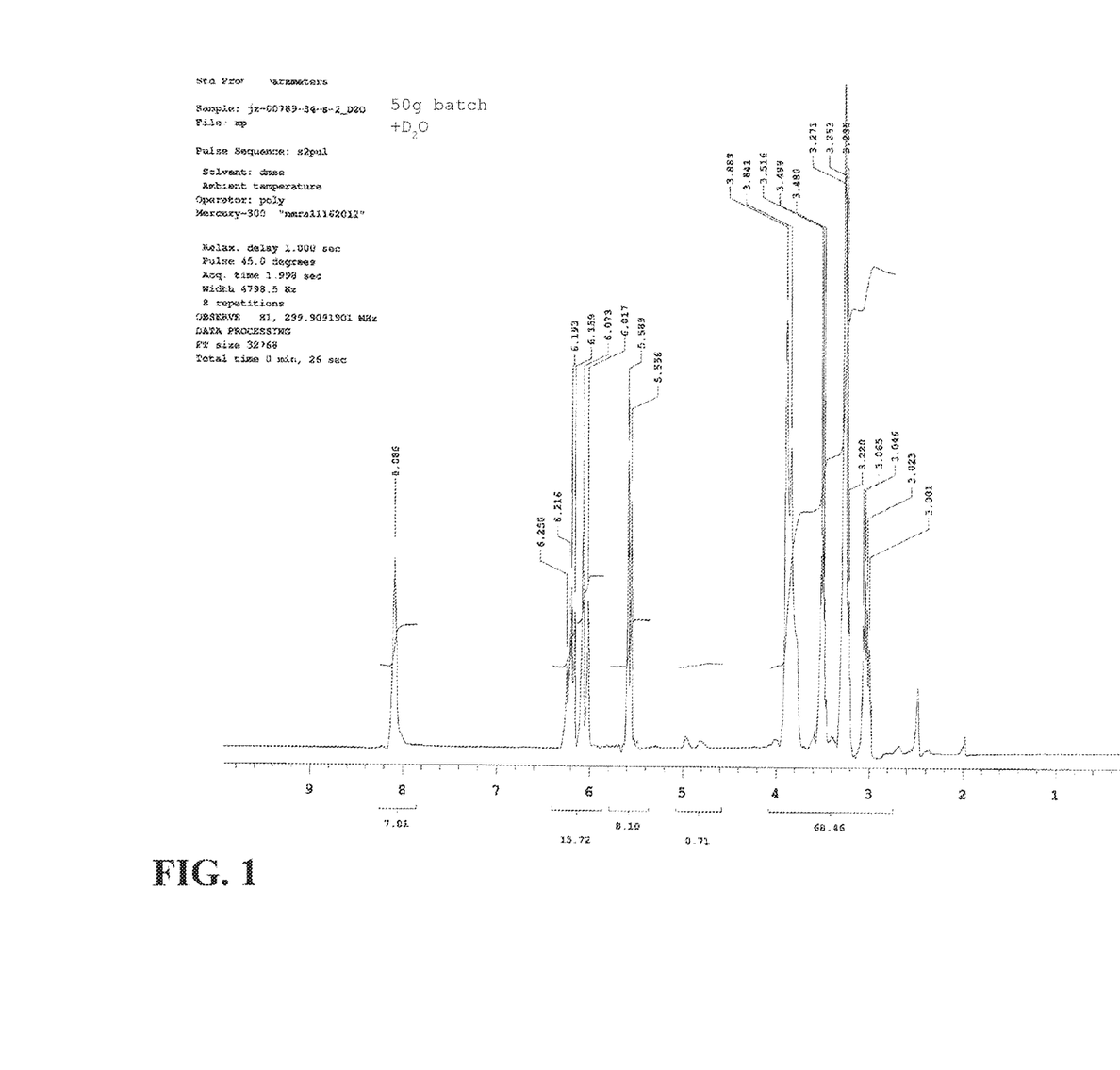
FIG. 1 and FIG. 1A are NMR of the acrylamide monomer formed in Example 1.
Figure 1A:
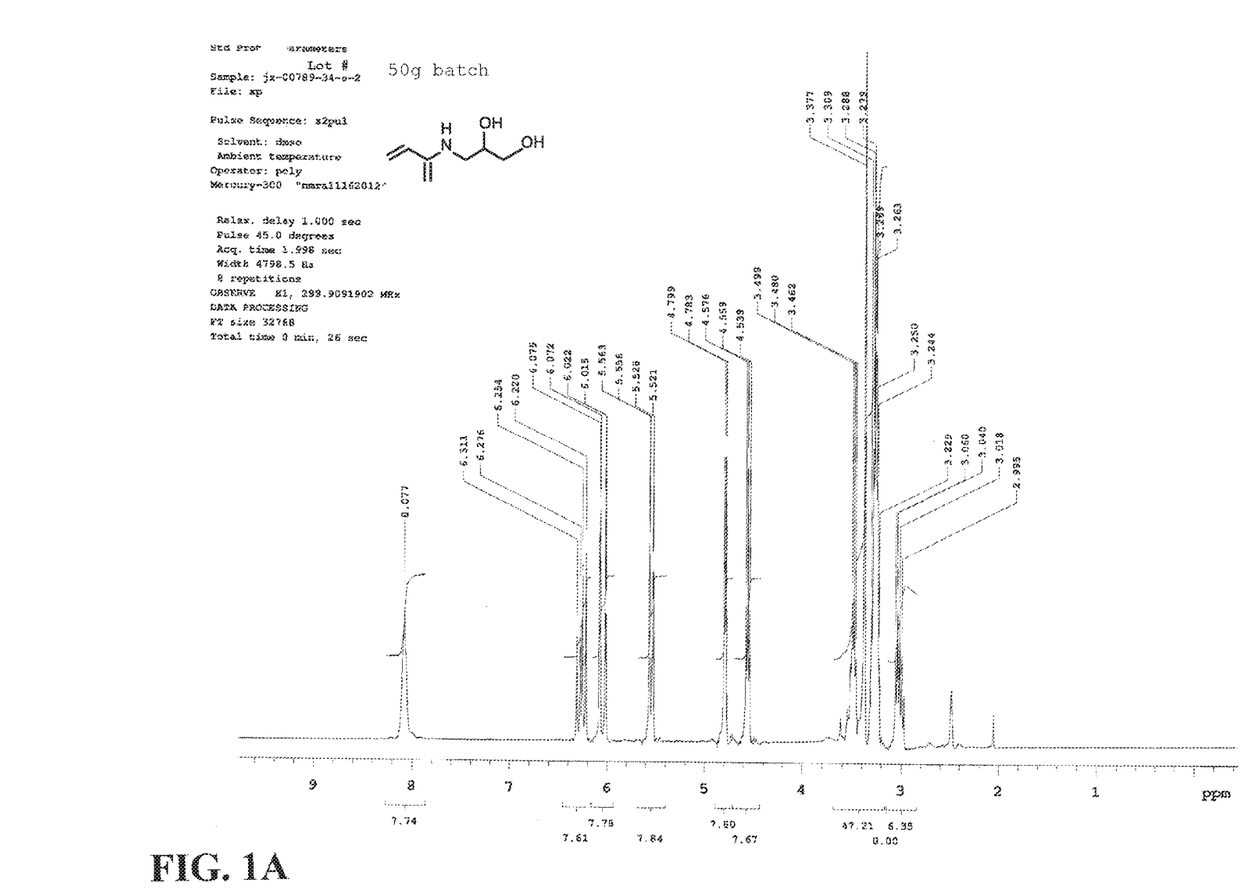

The bottom layer was extracted with 0.5 L of acetonitrile, repeating the above procedure (decantation, concentration, dilution, and filtration). Both acetonitrile solutions were combined and concentrated on a rotovap until heavy foaming began, resulting in a viscous colorless liquid (~50 g). The resultant monomer was obtained in high purity, as shown by the NMR in FIG. 1.

Example 2

Formulation of Methacrylamide Monomer

To a 1-L reactor charged 565 ml of anhydrous methanol under dry air flow, 3-amino-1,2-propanediol (from TCl, 50 g, 0.55 mol, 1 eq) is added portion-wise and stirred until fully dissolved (clear colorless solution). MEHQ (6 mg) and Sodium Carbonate (34.3 g) is added and the reactor was cooled (under vigorous stirring and air flow) to −10° C.

Methylacryloyl chloride (60.5 g, 0.67 mol, 1.2 eq) is added drop-wise over 2 h allowing temperature to slowly rise to +8° C., resulting in white milk-like suspension. The cooling bath is removed and temperature was raised to ambient (15-25° C.) over 1 h.

The resulting solids are filtered off and washed with methanol. The mother liquor is concentrated on a rotovap below 30° C. to approximately 100-150 ml volume. This residue is mixed with 0.5 L of acetonitrile (forming heavy bottom layer) and stirred for several hours.

The upper layer is decanted and concentrated to approximately ⅓ volume and diluted with 0.5 L of acetonitrile, followed by filtration through a pad of 40 g of silica gel.

Figure 2:
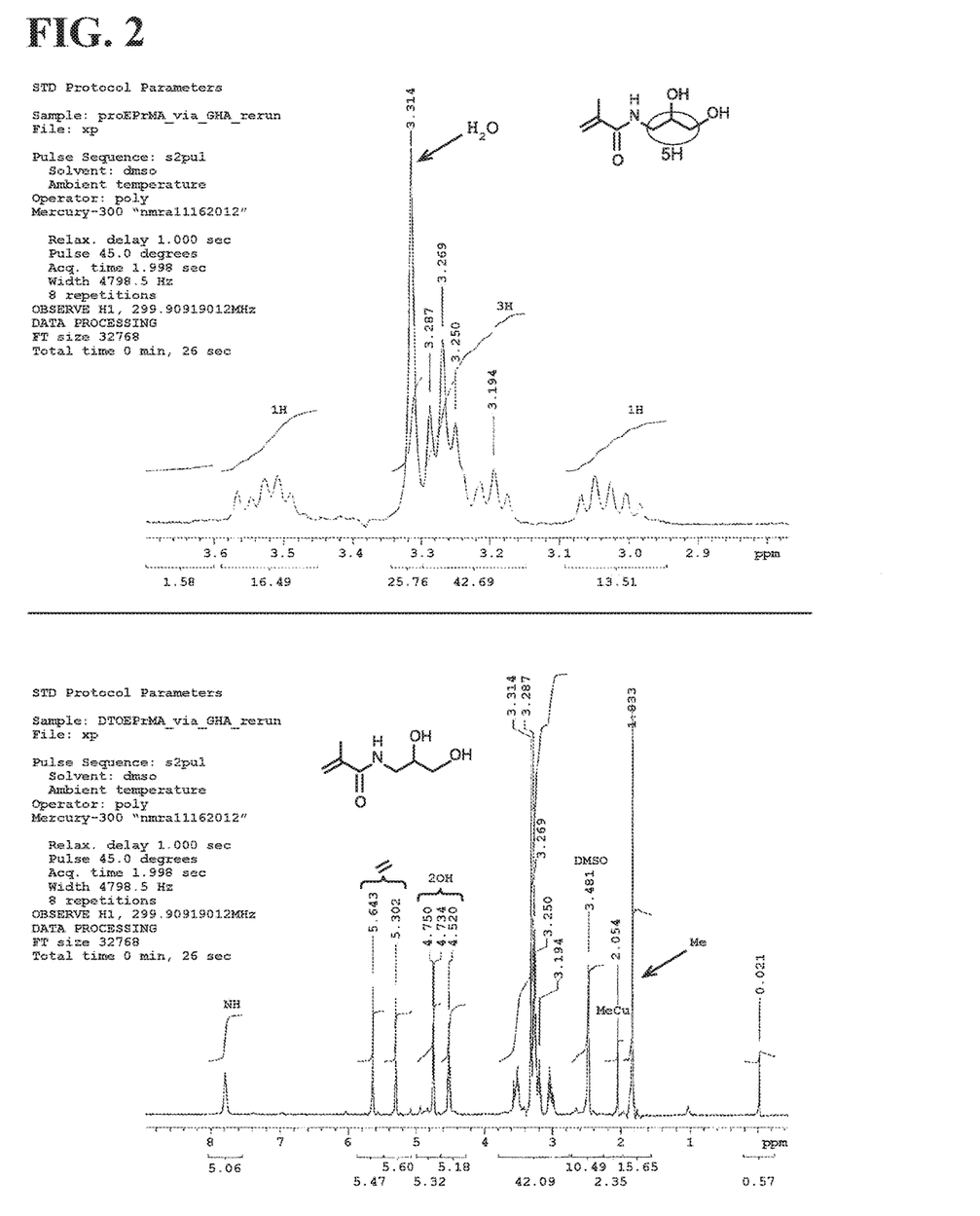
FIG. 2 is a NMR of the methacrylamide monomer formed in Example 2.

The bottom layer is extracted with 0.5 L of acetonitrile, repeating the above procedure (decantation, concentration, dilution, and filtration). Both acetonitrile solutions are combined and concentrated on a rotovap until heavy foaming began, resulting in a viscous colorless liquid (~50 g). The resultant monomer is obtained in high purity, as shown by the NMR in FIG. 2.

Example 3

Formulation of Polymer with DHPMAm

To a dihyroxypropylmethacrylamide, optionally Monomer 2 and crosslinker were added to a vessel charged with diluent. The monomer formulation was degassed by bubbling an inert gas into the solution followed by subjecting the solution under reduced pressure this procedure was repeated until the solution was virtually free of oxygen and dissolved reactive gases. The solution was stirred, and initiator was added. The mixture was cured at 60° C. for 600 minutes, and the resulting polymer was inspected for water content, haze and elasticity. The results are outlined below in Table 1.

TABLE 1

| Monomer 1 | Monomer 2 | Crosslinker | Initiator | Diluent | Water | Water Balance | Haze | Elasticity |
|---|---|---|---|---|---|---|---|---|
| DHPMAm (100%) | — | MBAm (1%) | V50 | DI (50%) | 84.0 | — | Clear | Very Low |
| DHPMAm (75%) | EOEAm (25%) | MBAm (1%) | V52 | NMP (50%) | 83.4 | — | Clear | Very Low |
| DHPMAm (75%) | EOEAm (25%) | HMBMa (1% mol swap) | V52 | NMP (50%) | 85.3 | — | Slight Haze | Very Low |
| DHPMAm (75%) | HPMAm | MBAm (1%) | V50 | DI (50%) | 85.6 | — | Clear | Very Low |
| DHPMAm (75%) | EOEAm (25%) | Si (1% mol swap) | V50 | NMP/DI (50%) | 83.2 | — | Slight Haze | Very Low |
| DHPMAm (75%) | EOLAm (25%) | HMBMa (0.5%) | V50 | NMP/DI (50%) | 83.1 | — | Slight Haze | Very Low |
| DHPMAm (75%) | DMA (25%) | HMBMa (0.5%) | V50 | NMP/DI (50%) | 84.7 | — | Clear | Very Low |
| DHPMAm (75%) | Am (25%) | HMBMa (0.5%) | V50 | NMP/DI (50%) | 83.7 | — | Clear | Very Low |
| DHPMAm (50%) | DMA (50%) | HMBMa (0.5%) | V50 | NMP/DI (50%) | 84.7 | — | Clear | Very Low |

TABLE 1-continued

| Monomer 1 | Monomer 2 | Crosslinker | Initiator | Diluent | Water | Water Balance | Haze | Elasticity |
|---|---|---|---|---|---|---|---|---|
| DHPMAm (50%) | Am (50%) | HMBMa (0.5%) | V50 | NMP/DI (50%) | — | — | — | — |
| DHPMAm (50%) | Am (50%) | MBAm (0.5%) | V50 | DI (50%) | 86.5 | — | Clear | Low |
| DHPMAm (50%) | Am (50%) | PEG3700 (0.5%) | V50 | DI (50%) | 87.5 | TBD | Clear | Moderate |
| DHPMAm (50%) | Am (50%) | PEG3700 (1.0%) | V50 | DI (50%) | 87.8 | 16.3 | Clear | Moderate |
| DHPMAm (50%) | Am (50%) | PEG3700 (1.5%) | V50 | DI (50%) | 88.1 | 14.4 | Clear | Moderate |
| DHPMAm (50%) | Am (50%) | PEG3700 (2.0%) | V50 | DI (50%) | TBD | TBD | | |
| DHPMAm (65%) | Am (35%) | PEG3700 (1.5%) | V50 | DI (50%) | TBD | TBD | | |

Example 4

Formulation of Polymer with DHPAm

To a dihyroxypropylacrylamide, optionally Monomer 2 and crosslinker are added to a vessel charged with diluent. The monomer formulation is degassed by bubbling an inert gas into the solution followed by subjecting the solution under reduced pressure this procedure is repeated until the solution is virtually free of oxygen and dissolved reactive gases. Initiator was added. The mixture is cured at 60° C. for 600 minutes, and the resulting polymer was inspected for water content, haze and elasticity. The results are outlined below in Table 2.

Example 5

(Meth)acrylamide Contact Lens Fabrication Procedure (Molding)

The monomer formulation is degassed to remove oxygen and dissolved gases before dispensing into the CL mold. 150 µL of the modified (meth)acrylamide monomer formulation (i.e., Monomer 1, Monomer 2, crosslinker, initiator and diluent) is dispensed into a female contact lens mold. The male mold half is placed inside the female to complete the mold assembly. The mold assemblies are placed into an oven and cured at 60° C. for 10 hours. The assemblies are removed and opened by removing the male mold half. The lenses are removed by allowing the (meth)acrylamide poly-

TABLE 2

| Monomer 1 | Monomer 2 | Crosslinker | Initiator | Diluent | Water | Water Balance | Haze | Elasticity |
|---|---|---|---|---|---|---|---|---|
| DHPAm (100%) | — | MBAm (1%) | V50 | DI (50%) | 85.0 | — | Clear | Very Low |
| DHPMAm (50%) | DHPAm (50%) | MBAm (1%) | V50 | DI (50%) | 84.0 | — | Clear | |
| DHPAm (75%) | EOEAm (25%) | MBAm (1%) | V52 | NMP (50%) | 83.4 | — | Clear | Very Low |
| DHPAm (75%) | EOEAm (25%) | HMBMa (1% mol swap) | V52 | NMP (50%) | 85.3 | — | Slight Haze | Very Low |
| DHPAm (75%) | HPMAm | MBAm (1%) | V50 | DI (50%) | 85.6 | — | Clear | Very Low |
| DHPAm (75%) | EOEAm (25%) | Si (1% mol swap) | V50 | NMP/DI (50%) | 83.2 | — | Slight Haze | Very Low |
| DHPAm (75%) | EOEAm (25%) | HMBMa (0.5%) | V50 | NMP/DI (50%) | 83.1 | — | Slight Haze | Very Low |
| DHPAm (75%) | DMA (25%) | HMBMa (0.5%) | V50 | NMP/DI (50%) | 84.7 | — | Clear | Very Low |
| DHPAm (75%) | Am (25%) | HMBMa (0.5%) | V50 | NMP/DI (50%) | 83.7 | — | Clear | Very Low |
| DHPAm (50%) | DMA (50%) | HMBMa (0.5%) | V50 | NMP/DI (50%) | 84.7 | — | Clear | Very Low |
| DHPAm (50%) | Am (50%) | HMBMa (0.5%) | V50 | NMP/DI (50%) | — | — | — | — |
| DHPAm (50%) | Am (50%) | MBAm (0.5%) | V50 | DI (50%) | 86.5 | — | Clear | Low |
| DHPAm (50%) | Am (50%) | PEG3700 (0.5%) | V50 | DI (50%) | 87.5 | TBD | Clear | Moderate |
| DHPAm (50%) | Am (50%) | PEG3700 (1.0%) | V50 | DI (50%) | 87.8 | 16.3 | Clear | Moderate |
| DHPAm (50%) | Am (50%) | PEG3700 (1.5%) | V50 | DI (50%) | 88.1 | 14.4 | Clear | Moderate |
| DHPAm (50%) | Am (50%) | PEG3700 (2.0%) | V50 | DI (50%) | TBD | TBD | | |
| DHPAm (65%) | Am (35%) | PEG3700 (1.5%) | V50 | DI (50%) | TBD | TBD | | | mer to hydrate and expand away from the mold in DI water. The lenses are allowed to hydrate overnight in saline to reach an equilibrium water content. The lenses are placed into vials containing fresh saline and autoclaved.

What is claimed is:

1. A contact lens or IOL comprising at least one polymer comprising
   a first monomeric subunit comprising a polymerized acrylamide or methacrylamide group, at least one side group comprising an aliphatic carbon moiety substituted by at least two hydroxyl moieties,
   a second monomeric subunit comprising a polymerized acrylate or methacrylate group, and
   a cross-linking monomeric subunit comprising a polymerized di(meth)acrylamide monomer,
   wherein the first monomeric subunit constitutes at least 50 wt. % of the polymer, and
   the polymer does not comprise an ionic moiety.

2. The contact lens of claim 1, wherein the side group of the first monomeric subunit comprises a branched or unbranched C3-5 aliphatic carbon moiety substituted by two hydroxyl moieties.

3. The contact lens of claim 1, wherein the cross-linking monomeric subunit constitutes greater than zero, but less than 5% of the polymer.

4. The contact lens of claim 1, wherein the side group of the first monomeric subunit is a 2,3-dihydroxylpropyl moiety.

5. The contact lens according to claim 1, wherein at least one polymer further comprises a polymerized UV absorbing monomer.

6. A contact lens blank, comprising a polymer formed from a mixture of monomers comprising a crosslinking monomer, a monomer comprising a polymerized acrylate or methacrylate group, and greater than about 50 wt. % of 2,3-dihydroxylpropyl (meth)acrylamide.

7. The contact lens blank according to claim 6, wherein the crosslinking monomer is a PEG di(meth)acrylamide.

8. The contact lens blank according to claim 6, wherein the contact lens further comprises water.

9. The contact lens blank according to claim 6, wherein the contact lens blank has an equilibrium water content of about 70 percent to about 75 percent.

10. The contact lens blank according to claim 9, wherein the contact lens blank is capable of being machined.

11. The contact lens blank according to claim 6, wherein the mixture of monomers further comprises a UV absorbing monomer.

12. A composition comprising a polymer formed from a mixture of monomers constitutes greater than 50 wt. % dihydroxylpropyl (meth)acrylamide and a second monomer comprising a polymerized acrylate or methacrylate group, wherein the mixture of monomers comprises greater than zero, but less than 5 wt. % of a di-functional (meth)acrylamide monomer and the polymer does not comprise an ionic moiety.

13. The composition of claim 12, wherein the mixture of monomers further comprises a UV absorbing monomer.

14. The composition of claim 13, wherein the polymer further comprises water.

15. The composition of claim 13, wherein the polymer is suitable for use in a contact lens or IOL.

16. The composition of claim 13, wherein the composition is suitable for use in a contact lens.

17. A lens comprising at least one polymer comprising, a first monomeric subunit comprising polymerized 2,3-dihydroxypropyl (meth)acrylamide and a second monomeric subunit comprising 2-hydroxyethylmethacrylate and optionally a crosslinking monomeric subunit.

18. The lens of claim 17, wherein the first monomeric subunit constitutes at least 50 wt. % of the polymer.

19. The lens of claim 17, wherein the crosslinking monomeric subunit is present, and is a PEG di(meth)acrylamide.

20. The lens of claim 17, wherein the 2,3-dihydroxypropyl(meth)acrylamide monomer subunits constitutes 50 wt. % to 60 wt. % of the polymer.

21. A polymer consisting of a first monomeric subunit comprising polymerized 2,3-dihydroxypropyl (meth)acrylamide, a second monomeric subunit comprising 2-hydroxyethylmethacrylate, and optionally one or more selected from the group consisting of a cross-linking monomeric subunit, a UV absorbing monomer, and a polymer initiator.

22. The polymer of claim 21, wherein the cross-linking monomeric subunit is present, and is a PEG di(meth)acrylamide.

23. The polymer of claim 21, wherein the polymerized 2,3-dihydroxypropyl (meth)acrylamide constitutes at least 50 wt. % of the polymer.

24. The polymer of claim 21, wherein the polymerized 2,3-dihydroxypropyl (meth)acrylamide constitutes 50 wt. % to 60 wt. % of the polymer.

25. The polymer of claim 21, wherein the cross-linking monomeric subunit constitutes greater than zero, but less than 5% of the polymer.

26. The polymer of claim 21, wherein the polymer has an equilibrium water content of about 70 percent to about 75 percent.

27. The contact lens of claim 1, wherein the contact lens further comprises water.

28. The contact lens of claim 27, wherein the contact lens has an equilibrium water content of about 70 percent to about 75 percent.

29. The contact lens of claim 1, wherein the first monomeric subunit constitutes 50 wt. % to 60 wt. % of the polymer.

* * * * *